(12) United States Patent
Thomas et al.

(10) Patent No.: US 8,153,231 B2
(45) Date of Patent: Apr. 10, 2012

(54) THIN WEB

(75) Inventors: Paul E. Thomas, Terre Haute, IN (US);
Timothy L. Clark, Sullivan, IN (US)

(73) Assignee: Tredegar Film Products Corporation, Richmond, VA (US)

(*) Notice: Subject to any disclaimer, the term of this patent is extended or adjusted under 35 U.S.C. 154(b) by 728 days.

(21) Appl. No.: 11/903,688

(22) Filed: Sep. 24, 2007

(65) Prior Publication Data
US 2009/0082746 A1 Mar. 26, 2009

(51) Int. Cl.
*B32B 3/24* (2006.01)
*A61F 13/512* (2006.01)

(52) U.S. Cl. .... 428/132; 604/383; 604/378; 604/385.01

(58) Field of Classification Search .................. 428/132; 604/383, 378, 385.01
See application file for complete search history.

(56) References Cited

U.S. PATENT DOCUMENTS

| | | | |
|---|---|---|---|
| 3,054,148 A | 9/1962 | Zimmerli | |
| 3,709,647 A | 1/1973 | Barnhart | |
| 3,814,101 A | 6/1974 | Kozak | |
| 3,989,867 A | 11/1976 | Sisson | |
| 4,151,240 A | 4/1979 | Lucas et al. | |
| 4,155,693 A | 5/1979 | Raley | |
| 4,252,516 A | 2/1981 | Raley et al. | |
| 4,319,868 A | 3/1982 | Riemersma et al. | |
| 4,388,056 A | 6/1983 | Lee et al. | |
| 4,695,422 A | 9/1987 | Curro et al. | |
| 4,726,976 A | 2/1988 | Karami et al. | |
| 4,839,216 A | 6/1989 | Curro et al. | |
| 4,878,825 A | 11/1989 | Mullane, Jr. | |
| 4,948,638 A | 8/1990 | Francis | |
| 4,950,511 A | 8/1990 | Francis | |
| 5,562,932 A | 10/1996 | Rieker | |
| 5,591,510 A | 1/1997 | Junker et al. | |
| 5,603,707 A | 2/1997 | Trombetta et al. | |
| 5,614,283 A | 3/1997 | Potnis et al. | |
| 5,674,211 A | 10/1997 | Ekdahl | |
| 5,718,928 A | 2/1998 | Rieker | |
| 5,731,061 A | 3/1998 | Bezier | |
| 5,814,389 A * | 9/1998 | Giacometti | 428/132 |
| 5,840,675 A | 11/1998 | Yeazell | |
| 5,887,543 A | 3/1999 | Williams et al. | |
| 5,897,543 A | 4/1999 | Francis | |
| 6,019,511 A | 2/2000 | Thomas et al. | |
| 6,168,849 B1 | 1/2001 | Braverman et al. | |
| 6,627,791 B1 | 9/2003 | Veglio et al. | |
| 7,229,002 B1 | 6/2007 | Burch, Jr. et al. | |
| 2004/0209042 A1 | 10/2004 | Peacock | |
| 2005/0112323 A1 | 5/2005 | Thomas | |

FOREIGN PATENT DOCUMENTS

| | | |
|---|---|---|
| DE | 19851778 A1 | 5/2000 |
| EP | 0215684 | 3/1987 |
| EP | 0535580 A1 | 4/1993 |
| GB | 2167304 A | 5/1986 |
| GB | 2262906 A | 7/1993 |
| WO | 97/03818 | 2/1997 |
| WO | 99/39674 | 8/1999 |

* cited by examiner

Primary Examiner — William P Watkins, III

(57) ABSTRACT

Embodiments of a thin web comprising a plurality of channels extending through the film are disclosed. The channels are in a substantially closed position but are capable of being in an open position to allow flow from the female side through the film to the male side. In certain applications, a greater pressure on the female side than the male side is capable of opening the channels. Embodiments may also include a thin web comprising a plurality of three dimensional apertures extending through the plastic film. The apertures may form a substantially closed channel defined by a sidewall and the channels being disposed at an angle greater than 70° with respect to a female side of the film. The thin web may be a plastic film or a thermoplastic film comprising a polyolefin, for example, or any other suitable material. The polyolefin may comprise at least one of polyethylene, polypropylene, low density polyethylene, or high density polyethylene, for example.

15 Claims, 13 Drawing Sheets

THIN WEB

FIELD OF THE INVENTION

The present invention is directed to thin webs and methods of forming thin webs. The thin webs comprise apertures configured as preferential flow valves capable of allowing substantially more liquid flow through the film in one direction than the other.

BACKGROUND

Vacuum formed films typically have a plurality of apertures that allow liquids and gases to pass through the film. Such films may be incorporated into disposable products, such as feminine hygiene products, diapers, incontinent products, hospital pads, bedding, breathable clothing and/or sleeping bag linings, for example. Such products are typically composite structures comprising a top sheet for use adjacent to the skin and an absorbent layer. An example of an apertured film for making disposable diapers is disclosed in U.S. Pat. No. 3,814,101, which is hereby incorporated by reference.

One method of forming apertures in thin webs or plastic film is by vacuum film forming, see U.S. Pat. No. 3,054,148 which is hereby incorporated by reference, for example. In this process, the plastic film lays on a rotating screen having a plurality of holes. The film passes over a vacuum chamber as the screen rotates creating a pressure differential on either side of the plastic film. The pressure differential causes the film to rupture at the holes in the screen to form the apertures. The holes in the screen may be in a specific pattern or shape that transfers onto the film in the process. In this process, the heated film is supported by a screen and a vacuum applied to the underside of the perforated screen. Holes are pulled in the film in the direction of the vacuum beneath the screen thereby forming tapered capillaries in the film.

Many methods and apparatuses for preparing plastic films comprising apertures have been developed, examples include U.S. Pat. Nos. 4,155,693; 4,252,516; 3,709,647; 4,151,240; 4,319,868; 4,388,056; 4,950,511; 4,948,638; 5,614,283; and 5,887,543, which are all hereby incorporated by reference.

Conventional vacuum film forming process may comprise extruding molten polymeric materials such as polyethylene or other polyolefin through a die to form a hot melt web or by laying a previously formed thin web or plastic film on a screen. The hot melt web of polymer lays on a rotating screen mounted on a stationary vacuum drum. The vacuum drum has an axial slot and a set of seals extending longitudinally along the length of its inside surface, beneath the area where the web of plastic impinges on the screen or molding element. A vacuum is pulled on the inside the screen to form the apertures in the film through the holes in the screen. After the aperture is formed, air flowing through the film cools the film and sets the shape of the aperture.

The physical shape of the screen determines the geometric pattern of apertures on the film and thus contributes to its aesthetic, tactile and mechanical properties. U.S. Pat. Nos. 5,897,543; 5,718,928; 5,591,510; and 5,562,932, which are all hereby incorporated by reference, describe films, screens, and methods of forming films having apertures that form capillaries extending through the film and the capillaries are disposed at an angle from about 5° to about 60° with respect to a plane that is perpendicular to a surface of the film. Accordingly, the films will have a masking characteristic such that the absorbent material is not as visible to a user as when the capillaries are perpendicular to the surface of the film.

There is a need for a thin web comprising apertures acting as preferential flow valves. There is a need for a thin web that provides a significantly greater resistance to flow of a liquid through the web in one direction as compared the flow of the same liquid in the opposite direction.

SUMMARY

Embodiments of the thin web may be useful as a separator in a container that is comprises two sections. Such a container could be used to separate a liquid from a solid such as fresh fruit from its juice. As the juice is released from fruit in one section of the container, the juice may flow through the separator comprising a thin web with preferential flow valves into another section of the container. The juice is then substantially trapped in the other section by the preferential flow valves in the thin web.

Embodiments include a thin web comprising a plurality of channels extending through the film, wherein the channels have a male side and a female side. The channels are in a substantially closed position and are capable of being in an open position to allow flow from the female side through the film to the male side. In certain applications, a greater pressure on the female side than the male side is capable of opening the channels. Further in other embodiments, that may require a lower degree of reverse flow, a greater pressure on the male side than the female side is capable of holding the channels in a substantially closed position. Reverse flow in this application is flow in an undesired direction such as, for example, from a section of a container containing released fruit juice to a section containing fruit.

Embodiments may also include a thin web comprising a plurality of three dimensional apertures extending through the plastic film. The apertures may form a substantially closed channel defined by a sidewall and the channels being disposed at an angle greater than 70° with respect to a female side of the film. In such embodiment, the sidewall may act as a flap to keep the aperture in a substantially closed position. The flap may react to pressure or weight that is capable of opening or further sealing the aperture as desired.

The thin web may be a plastic film or a thermoplastic film comprising a polyolefin, for example, or any other suitable material. The polyolefin may comprise at least one of polyethylene, polypropylene, low density polyethylene, or high density polyethylene, for example.

Details of embodiments of the thin web are described in the description below and the accompanying drawings. Other features and aspects of the invention may be apparent based upon an understanding of the features described and the non-limiting examples.

BRIEF DESCRIPTION OF THE FIGURES

FIG. 6b is a plan view and a side view of a forming screen suited for making the film embodiment of FIG. 6a;

FIG. 7b is a schematic illustration of a method of forming a screen having suited for use in making the film of FIG. 7a;

DESCRIPTION

The present invention is directed to thin webs comprising channels. The channels are capable of restricting flow in one direction to a much greater degree than other direction, such as by comprising preferential flow valves. In one embodiment, a thin web comprises a plurality of channels extending through the film. The channels may have a male side and a female side and are typically in a substantially closed position, however, are capable of being in an open position to allow flow from the female side through the film to the male side. Such channels may act as preferential flow valves in the thin web.

Figure 1:
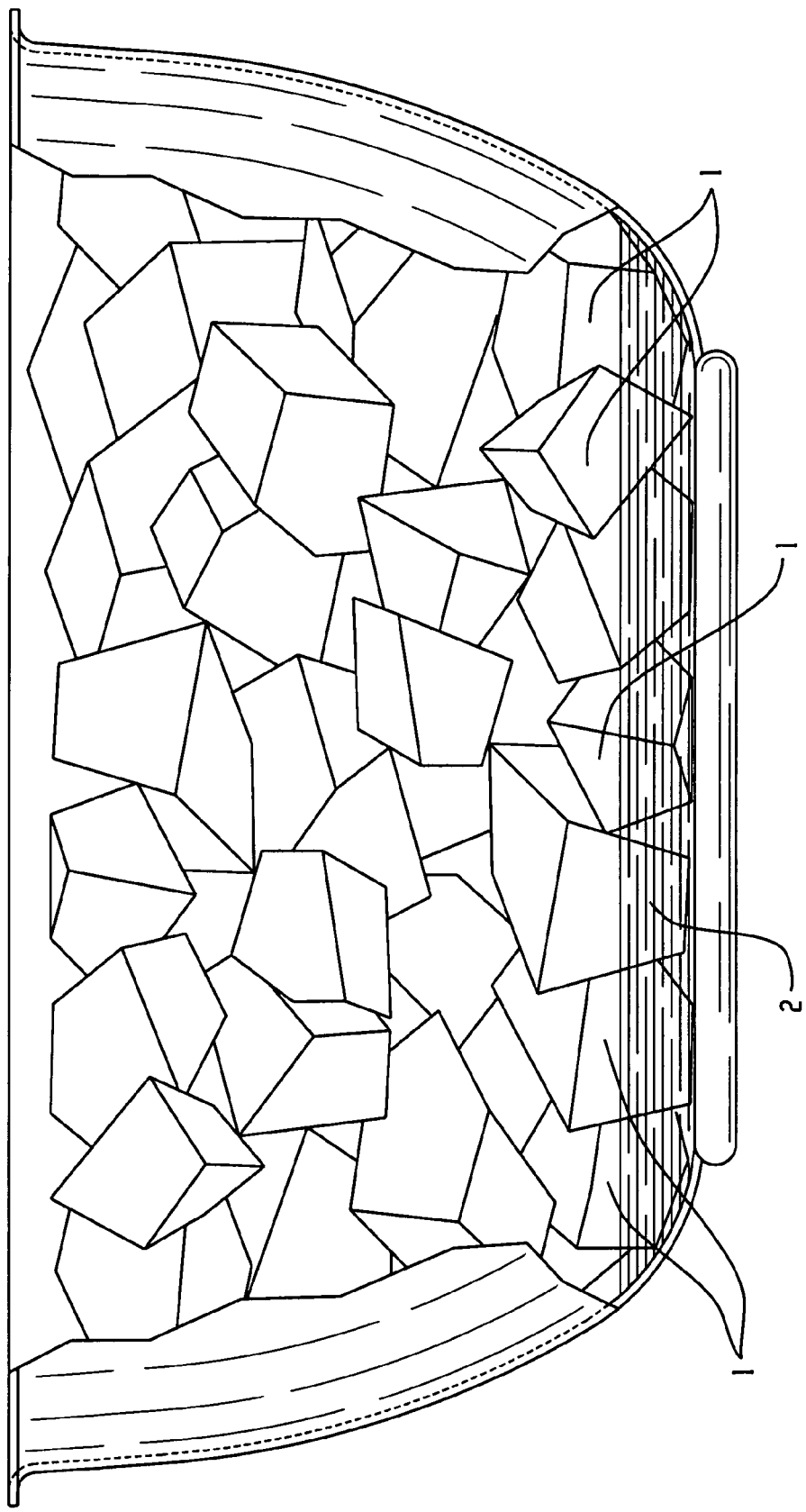
FIG. 1 is a side view of a container of fruit pieces sitting in fruit juices.

Embodiments of the thin web may be useful as a separator in a container that is comprises two sections. Such a container could be used to separate a liquid from a solid such as fresh fruit from its juice and prevent the liquid from substantially returning to the section containing the fruit. For example, as the fruit sits in the container on a shelf or in a refrigerator, juices may be released from the fruit. As shown in FIG. 1, fruit chunks 1 are in direct contact with juice 2 that was released from the chunks 1 after processing. Fruit sitting in juice or other liquids tend to reduce the apparent freshness and texture of the product. Additionally, the juice may contain or result in unwanted growth of undesired microorganisms or mold. Since this juice was released after storing the fruit, the fruit has not been pasteurized or other means have not been provided to prevent the growth of such undesirable microorganisms or molds.

Figure 2:
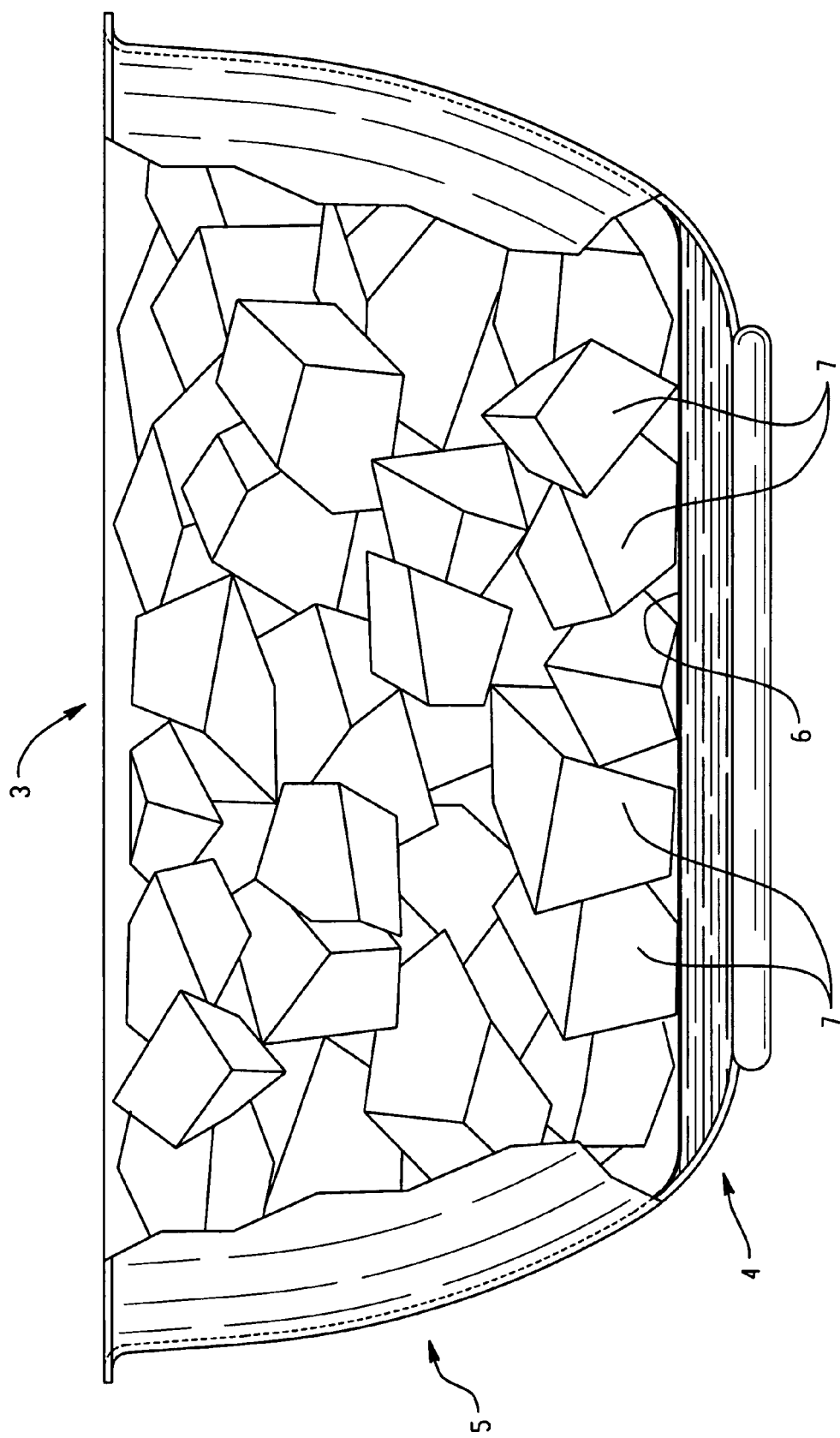
FIG. 2 is a side view of a container comprising a separation layer holding fruit pieces above the juices.

Embodiments of the thin web may comprise channels that are typically in a closed position but a greater pressure on the female side than the male side is capable of opening the channels. Embodiments of the channels may also be capable of being held in a closed position when exposed to a greater pressure on the male side than the female side. The pressure differential may be as a result of weight of an inanimate object, a living organism, any solid, liquid, and/or gas pressure on one side or the other. For example, the greater pressure may be caused by fruit, vegetables, meat products, insects, or a liquid such as water, fruit juice, vegetable juice, meat product juices, oils, as well as other substances. In one embodiment, the thin web may be used in a fruit container to keep the fruit separated from the juices released as the fruit is stored. As shown in FIG. 2, a container 3 comprises a lower section 4 and an upper section 5 separated by an embodiment of the thin web 6 comprising channels that are typically in a closed position but a greater pressure on the female side than the male side is capable of opening the channels. In such an embodiment, fruit 7 may be place in the upper section 5 of container 3 resting on the female side of the thin web 6. The weight of the fruit 7 on the thin web 6 may further open the channels to allow any liquid that may be released from the fruit to pass through the web 6 into the lower section 4 of container 3. The lower section 4 of the container 3 may be sized to contain all the liquid that may be released from fruit 7 during storage. The amount of liquid that is released is dependent on the kind of fruit, storage temperature, ripeness of the fruit, as well as other factors. Preferential flow valves on the thin web 6 substantially reduce the amount of liquid that will contact fruit 7 if container 3 is moved, tilted, dropped, or jostled, such as by handling, transporting, serving or other acts.

Without web 6 if container 3, is moved, tilted, dropped, or jostled, the juices in the bottom section 4 may contact fruit 7 in the upper section 5 causing transfer of any microorganisms or mold to the fruit. Embodiments of the thin web 6 significantly reduce the possibility of juices transferring from lower section 4 to the upper section 5 and potentially contaminating fruit 7. In FIG. 2, the fruit chunks 7 are held above the juice that was released from the fruit 7 during storage. The container 3 comprises a separation layer comprising an embodiment of the thin web 6 of the present invention. The fruit will remain fresher and safer for consumption for a longer period when it is not in contact with juice or other liquid.

Figure 3A:
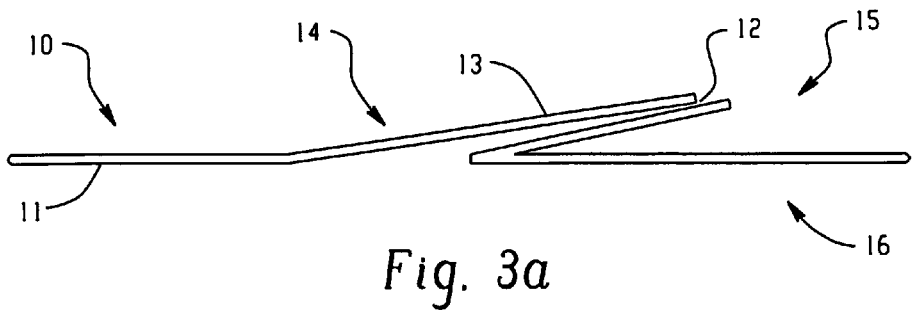
FIGS. 3a, 3b, and 3c are side views of an embodiment of a plastic film comprising channels disposed at an angle greater than 70° with respect to a female side of the film.
Figure 3B:
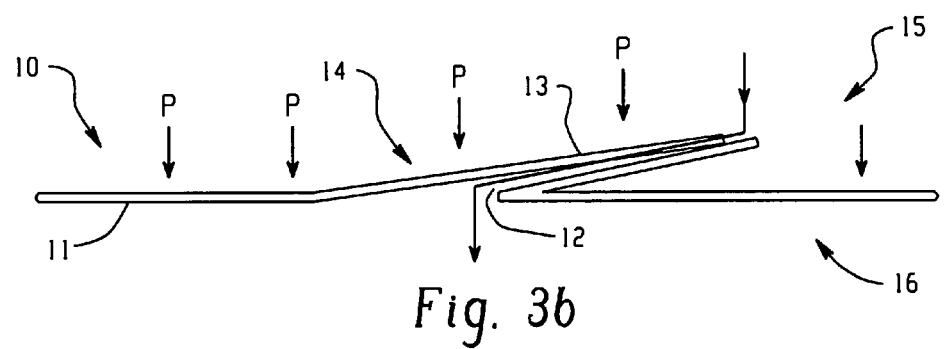
Figure 3C:
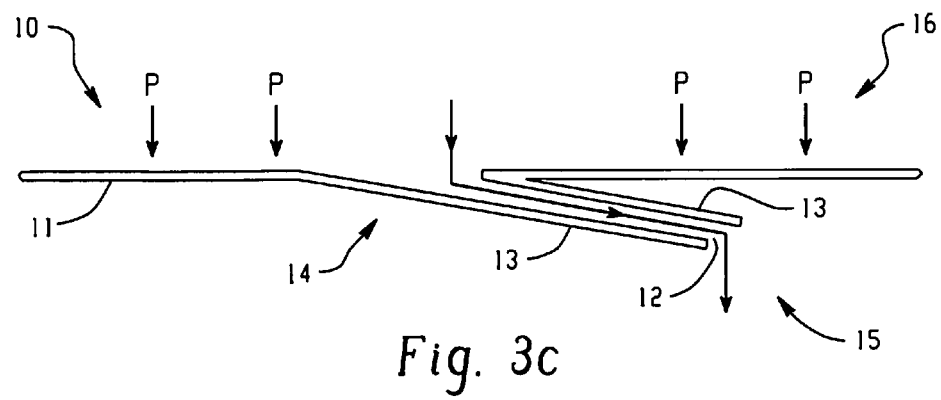

FIGS. 3a, 3b, and 3c depict embodiments of a thin web comprising channels being disposed at an angle greater than 70° with respect to a female side of the film. FIG. 3a depicts an embodiment of a thin web 10 wherein the pressure on the male side 15 and female side 16 of the thin web 10 are substantially the same. The sidewall 13 of channel 12 forms a flap 14 that is in a substantially closed position. Embodiments of the thin web have a memory that returns the web the flap 14 substantially to its original position after distortion of the web by a force such as a differential pressure or the weight of an object on the film. Of course, if a sufficiently strong force is exerted on the film, permanent deformation may occur. FIG. 3b depicts a portion of an embodiment of thin web 10 wherein there is a greater pressure on the male side 15 than the female side 16 of the thin web 10. This differential pressure is holding the channel 12 in a substantially more closed position than the channel 12 in FIG. 3a. FIG. 3c depicts a portion of an embodiment of a thin web 10 wherein there is a greater pressure on the female side 16 than the male side 15 of the thin web 10. A differential pressure in this direction, opposite to the direction of FIG. 3b, act to at least partially open the channel to allow fluids or gases to more easily pass through the web.

Figure 4A:
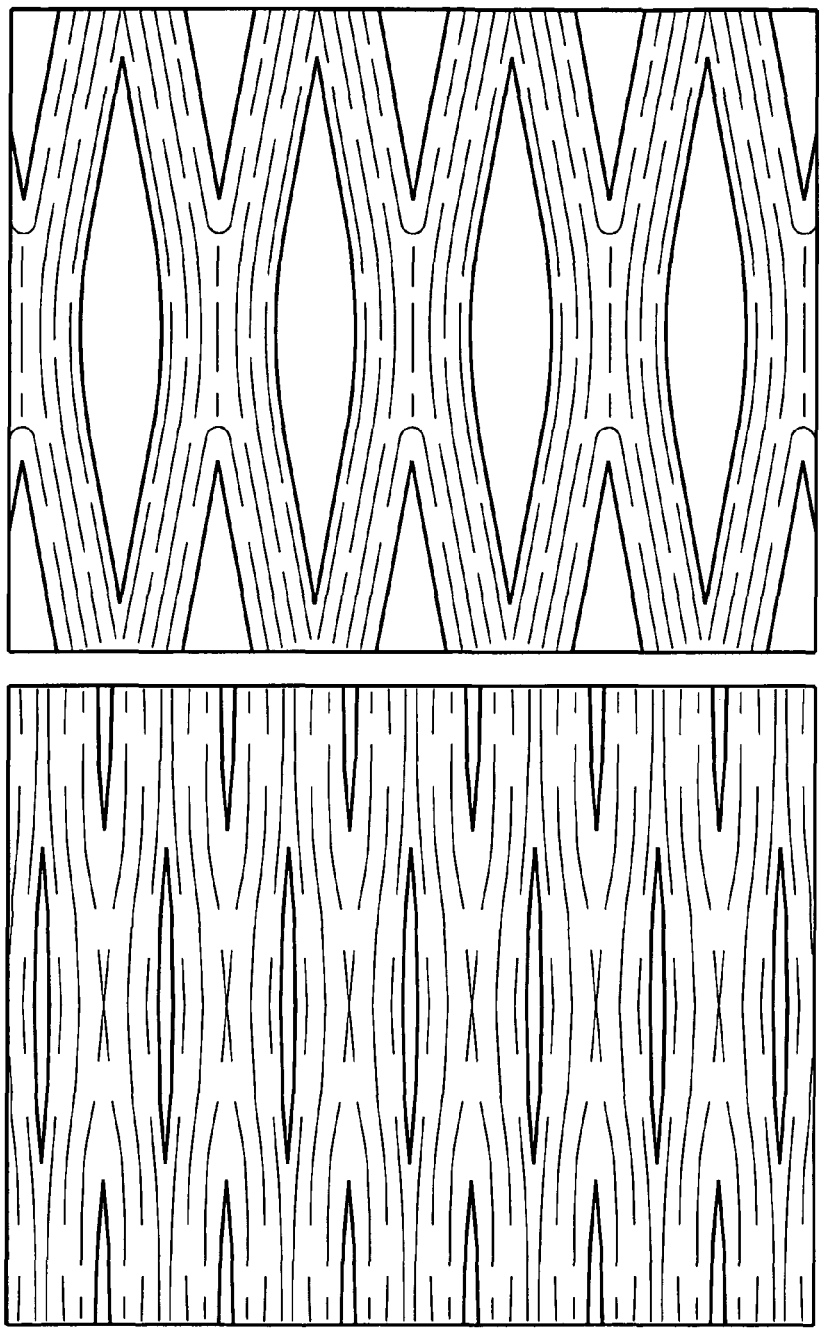
FIG. 4a is a plan view of an embodiment of a plastic film illustrating the channels from the female side of the film.
Figure 4B:
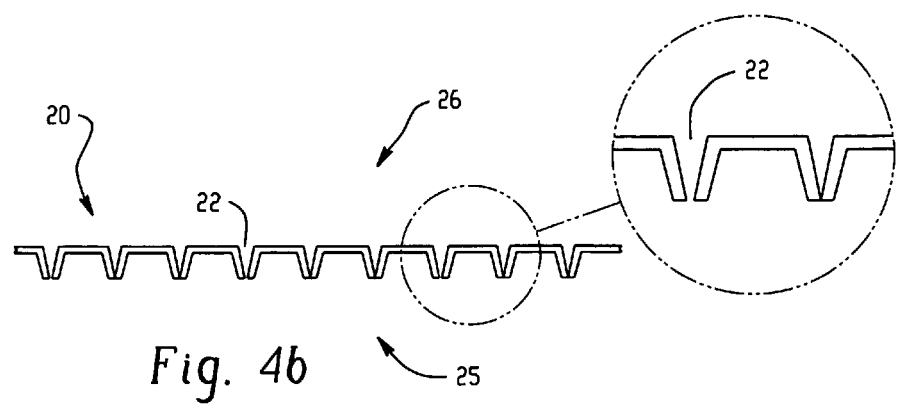
FIGS. 4b, 4c, and 4d are side views of an embodiment of a plastic film illustrating the effects on the channels from a pressure differential on either side of the film.
Figure 4C:
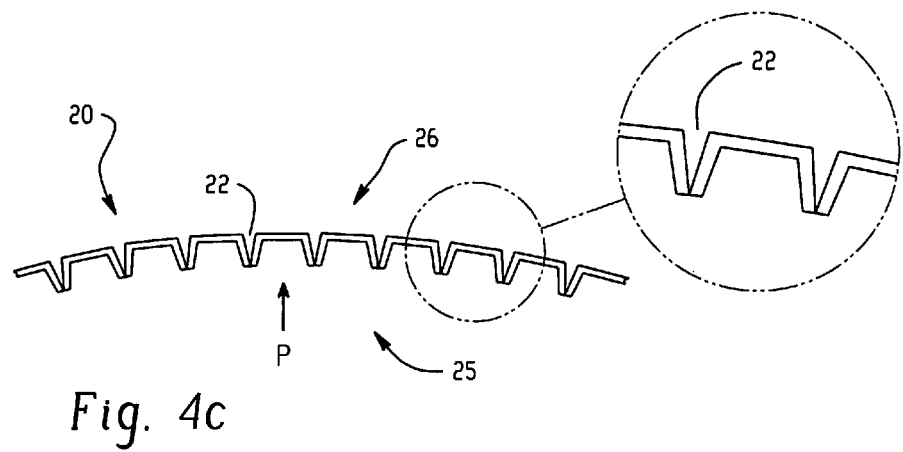
Figure 4D:
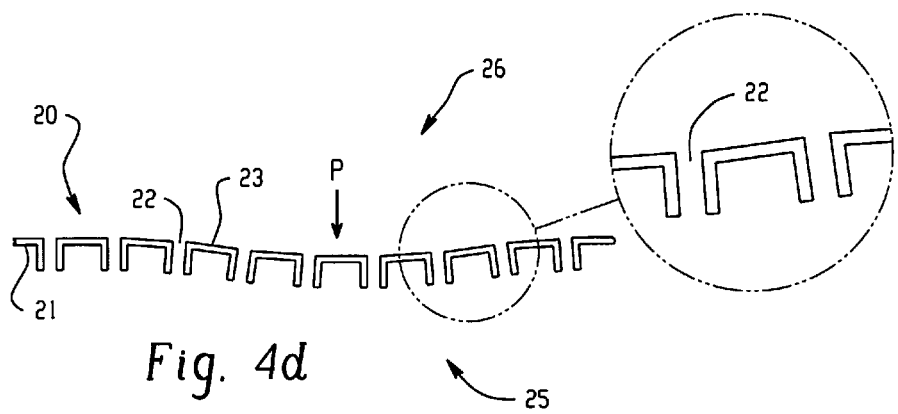

FIGS. 4a, 4b, 4c, and 4d depict embodiments of a thin web wherein the openings on the female side of the three dimensional apertures are in the shape of a slit. FIG. 4a is a plan view of an embodiment of the thin web showing the slits. FIG. 4b depicts a portion of an embodiment of the thin web 20 comprising a female side 26 of channels 22 is in the shape of a slit wherein the pressure on the male side 25 and female side 26 of the thin web 20 is substantially the same. A majority of the channels 22 are in a substantially closed position, but are capable of being in an open position to allow preferential flow from the female side through the film to the male side. The channels 22 are capable of being in an open position by deformation of the thin web, such as deformation by a differential pressure or weight of an object or liquid on the surface of the film. Preferably, the channels 22 of the web 20 are capable of being in an open position by a higher pressure or placement of an object or fluid on the female side 26 of the web. FIG. 4c depicts an embodiment of a thin web 20 wherein there is a greater pressure on the male side 25 than the female side 26 of the thin web 20. In this embodiment, the higher pressure on the male side 25 tends to hold the channels 22 in a substantially closed position. FIG. 4d depicts a portion of an embodiment of a thin web 20 wherein there is a greater pressure on the female side 26 than the male side 25 of the thin web 20. The higher pressure on the female side 25 causes the channels to open more thereby allowing liquids or other objects to pass through the channels 22.

The channels in the thin web may have any desired shape. The apertures are typically generally circular and, thus, the channel formed is generally cylindrical or conical in shape. However, the shape of the apertures and the channels can be any desired shape such as slit, oval, ellipsoidal, cat's eye, lens, rectangular with semicircular ends, and other shapes may be used. In addition, multi-sided shapes such as a triangular, rectangular, square, hexagonal or a pentagonal can be utilized for the openings to form the channel. If desired, any of the shapes of the apertures may have rounded corners to ease the production of the film. The apertures may be any size and have any desired aspect ratio (the ratio of major axis to minor axis), however, in some embodiments it may be advantageous for the aspect ratio of the apertures be in the range of from 4:1 to 2:1. More specifically, and in some embodiments comprising a cat's eye, lens, oval or rectangular shape with semicircular ends, it may be advantageous for the aspect ratio of the aperture to be about 3:1. In the embodiment wherein the aperture is a slit, the aspect ratio may be greater than 4:1. A further feature of the channel of embodiments of the preferential flow valve is that the channels may have an opening on the female side that is larger than an opening on the male side of the thin web. The larger opening on the female side may allow liquids to preferentially flow from the female side to the male side.

It may also be desirable in certain embodiments of the channel to comprise a flap. If the channels are disposed at an angle greater than 70° with respect to a female side of the film the sidewall of the channel may be considered to be a flap. A channel having a flap may be formed directly from the shape of the aperture in a screen or formed from the shape of the screen and a supplemental treatment such as folding the flap over in a nip, such as a heated nip or by tightly winding the web on a winding roll. Such a shape is an example of a preferential flow valve formed in the thin web.

The thin web may comprise a plastic or polymer and may be a plastic film. The plastic film may be any suitable material such as a plastic or thermoplastic film, such as a thermoplastic polyolefin. The polyolefin may comprise at least one of polyethylene, polypropylene, low density polyethylene, or high density polyethylene.

Figure 5B:
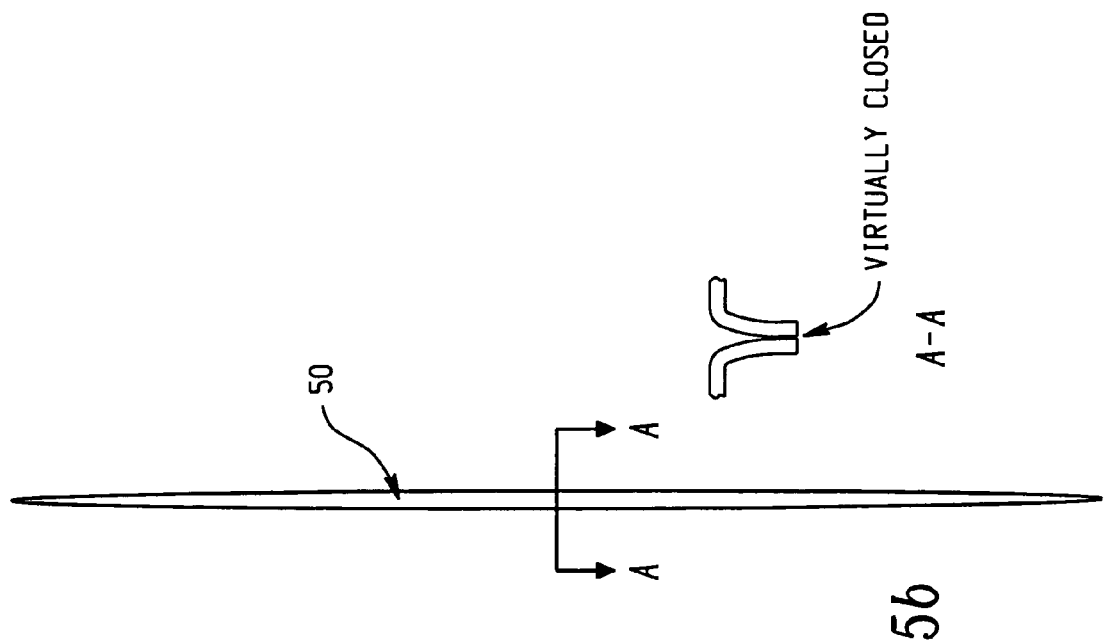
FIGS. 5a and 5b are plan views of a channel from the male side of a film and also show side views along line A-A
Figure 5A:
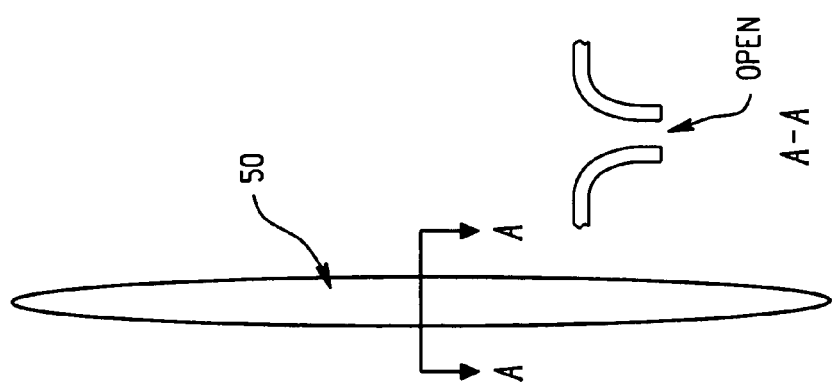

FIGS. 5a and 5b depict views from the male side of an embodiment wherein the aperture is in the shape of a slit. FIG. 5a shows a slit 50 in both plan view and a cross-sectional view in an open position. FIG. 5b shows the slit 50 both plan view and a cross-sectional view in a closed position.

Figure 6A:
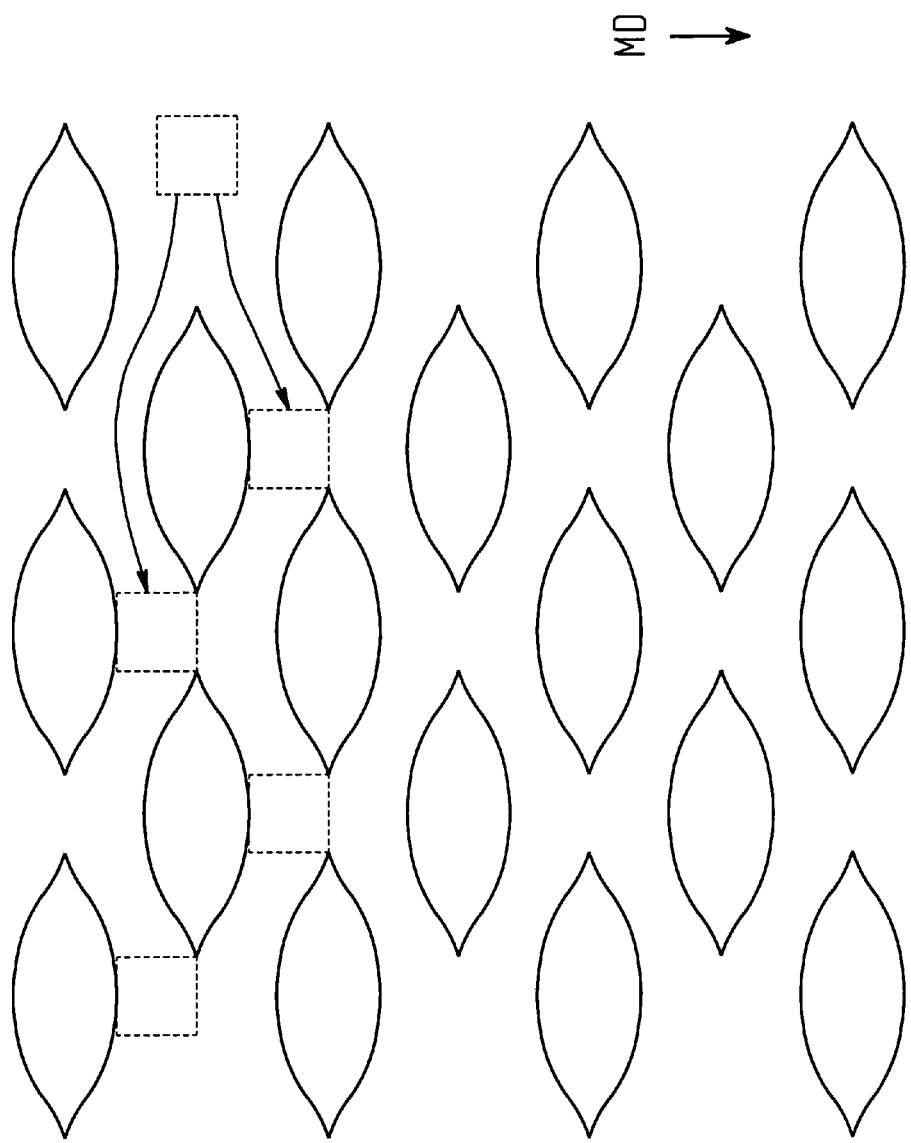
FIG. 6a is a plan view of an embodiment of a plastic film wherein the channel has a cat's eye or lens shaped opening when viewed from the female side.
Figure 6B:
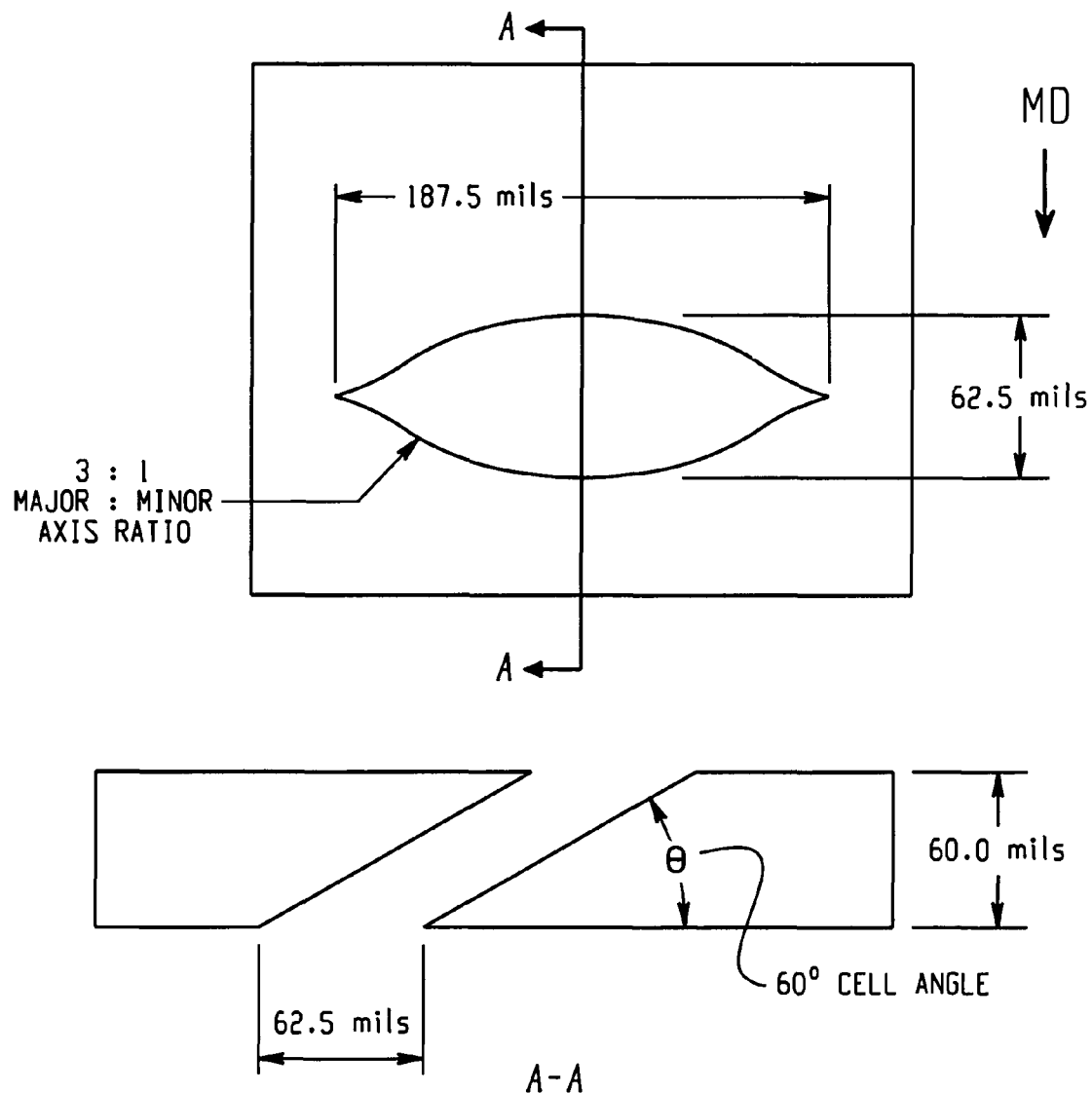

FIG. 6a depicts a plan view from the female side of an embodiment of a plastic film comprising a cat's eye or lens shaped aperture. The embodiment, as seen in FIG. 6b, shows one pattern that may be used to design the screen wherein a pattern array is established by a square imposed in the array as shown. The square maybe any size. In the embodiment of FIG. 6b the square is 62.5 mils. Additional patterns or spacing may be used as desired. The patterns and spacing will affect the open area of the thin web.

Figure 7A:
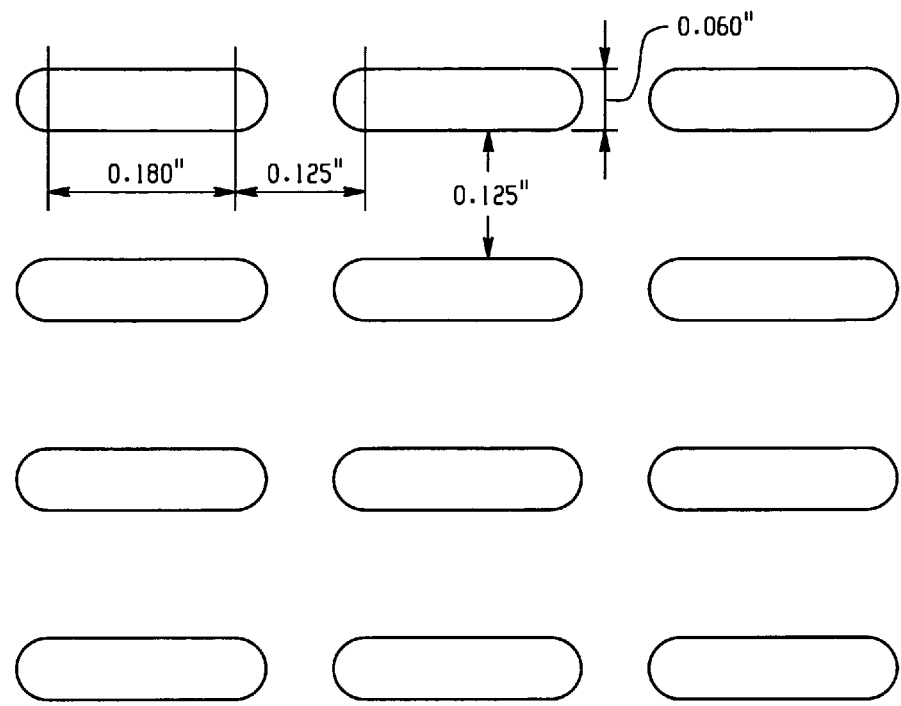
FIG. 7a depicts a plan view of a plastic film having a channel opening in the shape of an ellipse or a rectangle with semicircular ends when viewed from the female side.
Figure 7B:
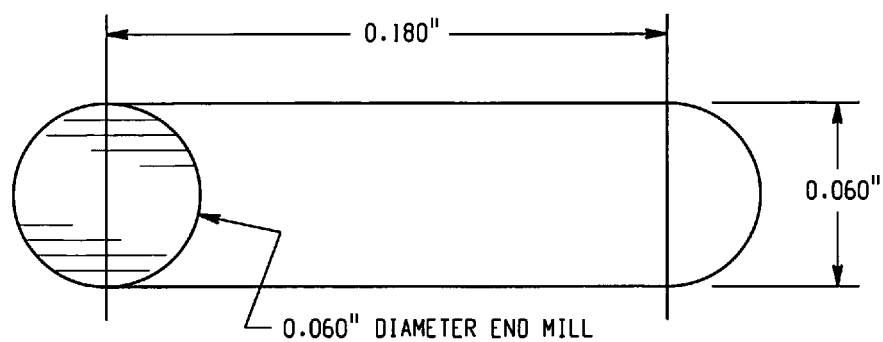

FIGS. 7a and 7b depict an embodiment of a plastic film, wherein FIG. 7a depicts a plan view of the plastic film comprising apertures having an elliptical shape or a shape of a rectangle with semicircular ends when viewed from the female side. In the embodiment of FIG. 7a the apertures are 0.06" wide and 0.192" wide. The apertures are spaced apart by 0.125" as shown. FIG. 7b depicts an aperture in a forming screen suited for making the film shown in FIG. 7a. In making the aperture in the forming screen, the end mill may enter the screen material at one point and move horizontally through the material to form the aperture of the desired shape, similar to a router. Alternatively, the end mill may be moved vertically into and out of the screen material in a drilling motion to form the aperture.

Figure 8A:
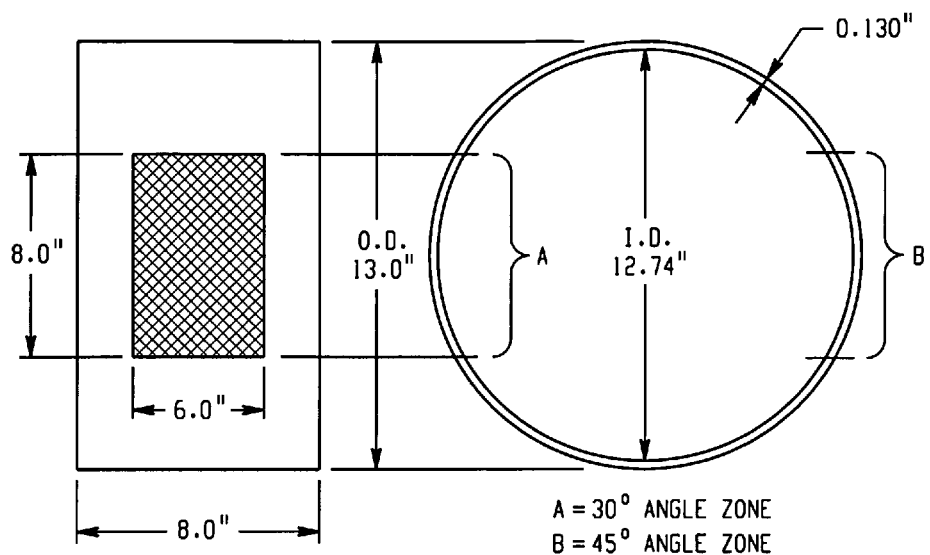
FIG. 8a shows a plan view and an end view of a forming screen that is suited for making a plastic film having channels oriented at 30° and 45°.
Figure 8B:
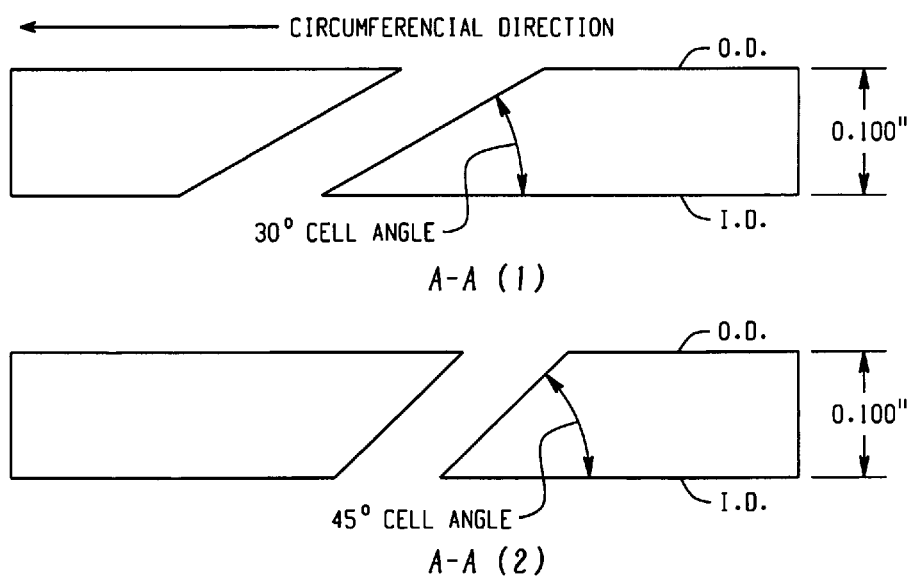
FIG. 8b is a side view of a forming screen showing the angles of the pathways in the screen of FIG. 8a for forming the channels in the film.

FIG. 8a depicts a screen that is capable of producing a film having channels angled at 30° and channels angled at 45° on the surface of the film. FIG. 8b are a cross sectional views of the screen showing apertures in the screen for forming the channels in the plastic film.

Figure 9:
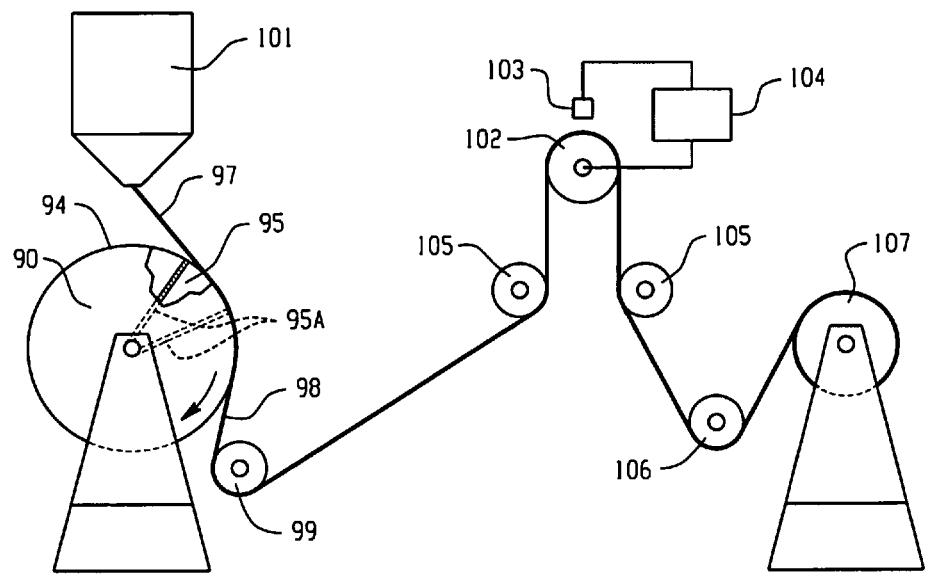
FIG. 9 is a schematic illustration of a process of making plastic films with channels.
Figure 10:
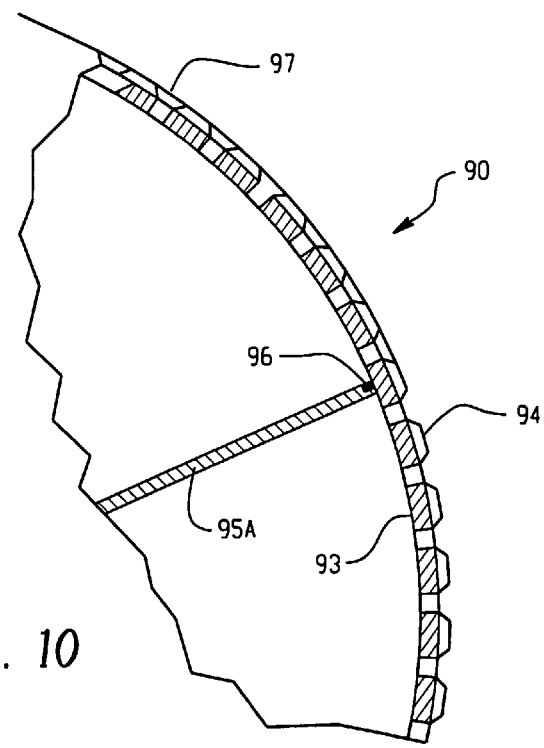
FIG. 10 is an enlarged sectional view of the vacuum drum and screen in the embodiment shown in FIG. 9.

Referring to FIGS. 9 and 10, an embodiment of an apparatus and method of forming the thin web comprises a rotary cylindrical drum 90. The cylindrical surface 93 of drum 90 comprises apertures to allow gases or liquids to flow from outside drum 90 to inside drum 90. A screen 94 is mounted on the surface 93 of drum 90 and rotates with the drum 90.

Screen 94 may be a cylinder that may be slipped on the drum 90 from an end or screen 94 may be wrapped around drum 90 and then affixed in any suitable manner. Various configurations of screens that may be used in embodiments of the present invention, some of which are described in U.S. Pat. No. 5,897,543, which is hereby incorporated by reference in its entirety. As shown in FIG. 9, a vacuum is created in the vacuum chamber 95 of drum 90 to cause a pressure differential between the inside and outside of the drum 90. A plastic sheet or a molten plastic film 97 is laid on the screen 94 and the differential pressure deforms the plastic film 97 into the apertures of the screen and causes similar apertures to be formed in the film.

The vacuum chamber 95 is positioned within drum 90 and opens at the surface of the drum over a limited portion of its periphery. Two plates 95A may be used to define the vacuum chamber 95. In order to provide an effective seal of the leading and trailing edges of vacuum chamber 95, seals 96 are typically provided in plates 95A. The seals may be made of metal, HDPE, rubber or other suitable material. The plates 95A are stationary with respect to the rotational direction of the drum and remain in a fixed or stationary position in drum 90. Thus, vacuum chamber 95 is sealed except the peripheral openings on drum 90 and may be evacuated or reduced in pressure by pumping equipment connected to the chamber in any suitable manner.

An extruder 101 may be located adjacent to drum 90 having a die which is used to extrude a hot web 97 onto screen 94. Polyolefins may be used for a thermoplastic film that may be extruded onto screen 94. The web 97 contacts screen 94 which is turning with drum 90. The rotating screen 94 carries sheet 97 over vacuum slot 95 which causes the web or thermoplastic film to be drawn into the openings in screen 94 and thereby apertured.

Optionally, from roll 99 the vacuum formed film 98 may continue to a roll and to corona treating roll 102. The corona treating roll 102 is usually covered with a suitable dielectric material such as epoxy, fluorinated polyethylene, chlorinated polyethylene, or polyester. However, bare roll treating with a dielectric covered electrode can be utilized to treat a film. The electrode or corona bar 103 is suspended parallel to the treating roll 102 at about 1/16 of an inch above the roll 102. The corona bar 103 is energized by a transformer and corona treating power source 104. The sheet may continue past a tension roll 105 to a second tension roll 106 and onto wind-up roll 107. It should be understood that the corona treating operation is not required for embodiments of the method of forming the web. Further, it is not always necessary to wind the web onto a wind-up roll 107 if the web is being put into an end use application in an in-line process. However, winding the web tightly on a windup roll may urge the preferential flow valve into more of a closed position and produce a web with a better memory for a closed position. As such, the web 98 may be tightly wound on the wind-up roll 107. Winding the film tightly may curve the channels or flaps of the film further into a closed position.

It should be noted that other forming processes can be utilized to form the perforated plastic films of the present invention. The process shown in U.S. Pat. No. 4,878,825 which utilizes a support for the forming screen in the area of the vacuum slot works particularly well in forming the perforated film of the present invention. The process shown in U.S. Pat. No. 4,839,216 that utilizes a high-pressure liquid stream to perforate a plastic film can be also used with the present invention. The teachings of U.S. Pat. Nos. 4,878,825 and 4,839,216 are hereby incorporated by reference into this patent application as alternative methods for forming the perforations of the present invention.

Embodiments of the plastic films may have capillaries that are disposed at an angle that acts to restrict the flow of liquids in one direction through the apertures. Accordingly, the films will have a characteristic such that fluids that pass through one direction and restricted in passing through one direction are restricted in passing through the plastic film in the reverse direction. The degree of restriction through the film will be affected by the angle of the capillaries in the film, their length and the degree to which the capillaries converge in shape. The plastic film of the present invention reduces the amount of the fluid will pass through the channels by splashing.

Figure 12A:
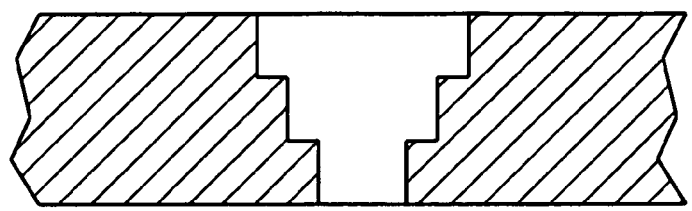
FIGS. 12a, 12b, 12c, and 12d are sectioned views forming screens that may be used in the embodiments.
Figure 12B:
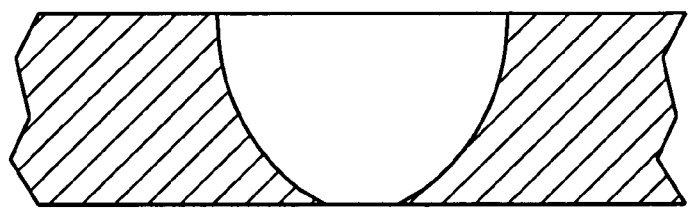
Figure 12C:
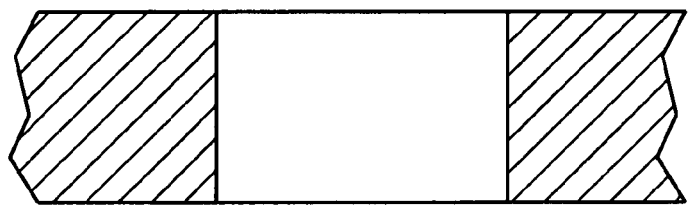
Figure 12D:
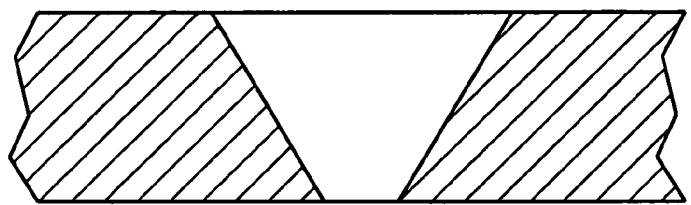

FIGS. 12*a*, 12*b*, 12*c*, and 12*d* depict embodiments of a screen that may be used in methods of forming a thin web. FIG. 12*a* depicts a cross section of a screen comprising an aperture having a step tapered profile. The step taper of the aperture in FIG. 12*a* is shown to be symmetrical and have even steps. Neither of these properties is required and the cross section of the aperture may be asymmetric or have any desired step size. FIG. 12*b* depicts a cross section of a screen comprising an aperture having a curved tapered profile. Embodiments of the wall profile of the curved taper aperture may be any curved shape including portions of circular, elliptical, parabolic, or any other curve. Curve sections may also be combined with linear profile of the step type to form a hybrid wave, or be a convex or concave. FIG. 12*c* shows an embodiment of a block profile without a taper. FIG. 12*d* depicts a cross section of a screen having a conical wall profile. The conical profile may comprise a truncated cone (as shown in FIG. 12*d*), or funnel shape (such as combining a conical profile and a block profile). The profiles illustrated are merely examples and may be modified in embodiments of the thin web.

Figure 11:
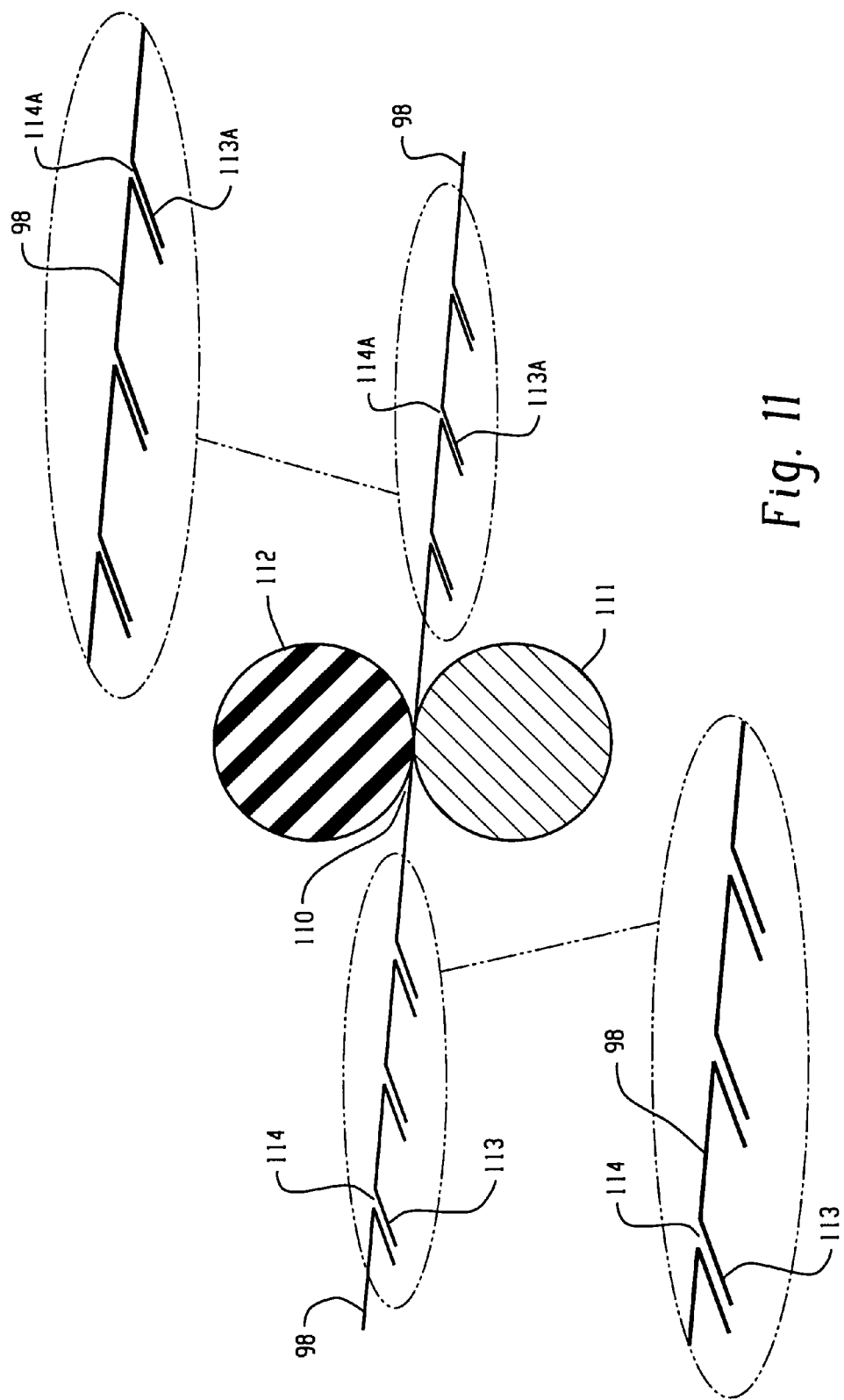
FIG. 11 is a schematic illustration of an optional method step wherein the preferential valves are modified by passing the thin web through a heated nip.

An additional step may be incorporated into the embodiment of the method shown in FIGS. 9 and 10. As shown in FIG. 11, the method may further include a step wherein the vacuum formed film 98 is passed through a nip 110 comprising at least one heated roller 111. The second roller 112 may be non-heated. This step causes the valve flaps 113 or channels 114 to assume a more permanent memory of being in a closed position. The memory in the film 98 causes the channel 114 and 114A to revert to the closed position after the differential pressure or other motive force is released.

Whereas compression of the channel in film 98 in the windup roll 107 also affects the memory position of the channels 114, compression relies on creep to occur in the plastic to set the channel in a closed memory position. Applying heat in the nip 110 of a heated roller 111 and 112 softens the polymer such that it will respond more effectively to the stresses applied to it between the rollers, or by other means, to cause it to adopt the new structural memory position 113A and 114A.

In one embodiment of the method of forming the plastic film, the film 98 passes through the nip 110 of the heated roller 111 with the flap 113 or channel 114 pointing away from the nip such that the end of the flap 113 or channel 114 enters the nip 110 last. By entering the nip 110 in such a direction the flap 113 or channel 114 will be pressed down toward the film 98 effectively to a substantially closed position of the flap 113A or channel 114A. This will cause the finished angle of the channel to become greater than 70 regardless of the initial angle of the film formed by the screen in the vacuum forming process.

EXAMPLE 1

A plastic jar with a screw-on lid was modified to provide a reversible flow container. A piece of plastic film is screwed into the lid. A beaker was filled with tap water to 150 ml line. Upon pouring the water into the device a stop watch is started. When the water has drained to the line denoting 100 ml of evacuation, the stop watch is stopped and the time, in seconds, was recorded. Five different film sample areas are tested to derive the averages above.

The drain portal is 1.75 inches in diameter or 2.4 square inches of area. By converting ml to Fluid Ounces the above average flow rates are calculate.

| Prior Art Ellipsoidal | | |
|---|---|---|
| Loft, mils | Flow Side, seconds | Closed Side, seconds |
| 43.5 | 0.8 | 7.4 |
| | Flow Side, Fl Oz/sec-in$^2$ | Closed Side, Fl Oz/sec-in$^2$ |
| | 1.76 | 0.19 |
| Inventive Preferential Flow Film | | |
| Loft, mils | Flow Side, seconds | Closed Side, seconds |
| 30.7 | 5.8 | 20.6 |
| | Flow Side, Fl Oz/sec-in$^2$ | Closed Side, Fl Oz/sec-in$^2$ |
| | 0.24 | 0.07 |

EXAMPLE 2

Faucet Drip Test: A faucet was set for dripping at 50 ml in 10 seconds (5 ml/sec). Film comprising preferential flow valves was placed over a beaker in the flow side and the closing side position. Beaker was placed under the faucet with valve angle pointing south. Beaker was tilted West at approximately 5° so the water could flow off if it did not penetrate the film layer. The film-covered beaker was exposed to the dripping for 10 seconds.

| Film comprising ellipse shaped valve | | | | | | | |
|---|---|---|---|---|---|---|---|
| | Valved Cell Features and Dimensions | | | | Gauge | Fluid Performance | |
| | Loft (μm) | Air Porosity Flow Side (CFM) | Air Porosity Closing Side (CFM) | Major Axis Flow Side (mm) | Minor Axis Flow Side (mm) | Basis Wt (Film Gauge) (GSM) | Faucet Drip* Flow Side (gms) | Faucet Drip* Closing Side (gms) |
| 1 | 709 | 161 | 102 | 6.58 | 4.40 | 37.9 | 37.3 | 8.5 |
| 2 | 687 | 172 | 98 | 6.82 | 4.69 | | 36.3 | 7.6 |
| 3 | 627 | 182 | 101 | 6.69 | 4.74 | | 41.8 | 3.8 |
| Avg | 674 | 172 | 100 | 6.70 | 4.61 | 37.9 | 38.5 | 6.6 |
| St Dev | 42.4 | 10.5 | 2.1 | 0.1 | 0.2 | | 2.93 | 2.495 |

A number of embodiments of the invention have been described. Nevertheless, it will be understood that various modifications may be made without departing from the scope of the invention. Accordingly, other embodiments are within the scope of the following claims.

The invention claimed is:

1. A thin web, comprising:
a single ply web having a plurality of channels extending through the web, wherein the channels comprise hollow tubular-shaped members having a male side and a female side, wherein the channels are normally in a substantially closed position and are disposed at an angle of greater than 70° relative to a plane that is perpendicular to a surface of the web; wherein a greater pressure on the female side than the male side is capable of opening the channels and a greater pressure on the male side than the female side is capable of holding the channels in a closed position.

2. The thin web of claim 1, wherein the female side of the channels contains an opening in the shape of an ellipse, a circle, or a rectangle with semicircular ends.

3. The thin web of claim 2, wherein the opening has a major axis and a minor axis and the ratio of the major axis to the minor axis is from 4:1 to 2:1.

4. The thin web of claim 3, wherein ratio of the major axis to the minor axis is about 3:1.

5. The thin web of claim 1, wherein the female side of the channels has an opening in the shape of a slit.

6. The thin web of claim 1, wherein the female side of channels has an opening in the shape of a cat's eye.

7. The thin web of claim 6, wherein the opening has a major axis and a minor axis and the ratio of the major axis to the minor axis is from 4:1 to 2:1.

8. The thin web of claim 7, wherein ratio of the major axis to the minor axis is about 3:1.

9. The thin web of claim 6, wherein at least end of the cat's eye is rounded.

10. The thin web of claim 1, wherein the web is one of a plastic film or a thermoplastic film comprising a polyolefin.

11. The thin web of claim 10, wherein the polyolefin comprises at least one of polyethylene, polypropylene, low density polyethylene, or high density polyethylene.

12. The thin web of claim 1, wherein an opening on the female side of the channel is larger than an opening on the male side of the channel.

13. The thin web of claim 1, wherein at least a portion of a sidewall of the channel acts as a flap to maintain the channels in a substantially closed position.

14. The thin web of claim 13, wherein an opening on the female side of the channel is larger than an opening on the male side of the channel.

15. A thin web, comprising:
a single ply web having a plurality of channels extending through the web, wherein the channels comprise hollow tubular-shaped members having a male side and a female side; wherein the channels have a cat's eye shape when viewed from the female side; said cat's eye shape defined by a major axis oriented parallel to a cross direction of the web and a minor axis oriented parallel to a machine direction of the web; wherein the ratio of the major axis to the minor axis is in the range of 4:1 to 2:1; wherein said tubular shaped members comprising said channels are oriented at an angle to a plane defined by the female side of the channels such that said tubular members form flaps that are in a substantially closed position; wherein a greater pressure on the female side than the male side is capable of opening the flaps and a greater pressure on the male side than the female side is capable of holding the flaps in a closed position.

\* \* \* \* \*